US012714501B2

(12) United States Patent
Neukirchen et al.

(10) Patent No.: US 12,714,501 B2
(45) Date of Patent: Aug. 25, 2026

(54) OPTIMIZATION IN ABLATION TREATMENT PLANNING

(71) Applicant: KONINKLIJKE PHILIPS N.V., Eindhoven (NL)

(72) Inventors: Christoph Neukirchen, Aachen (DE); Alfonso Agatino Isola, Eindhoven (NL); Marco Baragona, Delft (NL); Zoi Tokoutsi, Eindhoven (NL); Martijn De Greef, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1016 days.

(21) Appl. No.: 17/944,287

(22) Filed: Sep. 14, 2022

(65) Prior Publication Data

US 2023/0080805 A1 Mar. 16, 2023

Related U.S. Application Data

(60) Provisional application No. 63/244,786, filed on Sep. 16, 2021.

(51) Int. Cl.
*A61B 34/10* (2016.01)

(52) U.S. Cl.
CPC ........ *A61B 34/10* (2016.02); *A61B 2034/104* (2016.02)

(58) Field of Classification Search
CPC .............. A61B 34/10; A61B 2034/104; A61B 18/1206; A61B 2034/105
See application file for complete search history.

(56) References Cited

U.S. PATENT DOCUMENTS 11,123,046 B1 * 9/2021 Zohar .................. A61B 8/0891
2014/0201669 A1 7/2014 Liu
2018/0235686 A1 * 8/2018 Sahakian ............ A61B 18/148
(Continued)

FOREIGN PATENT DOCUMENTS

WO WO2019145211 A1 8/2019

OTHER PUBLICATIONS

Arora D. et al., “Model-Predictive Control of Hyperthermia Treatments”, IEEE Transactions On Biomedical Engineering, vol. 49, No. 7, pp. 629-639, Jul. 2002.
(Continued)

*Primary Examiner* — Joel Lamprecht

(57) ABSTRACT

A computer-implemented method of providing optimized values of treatment parameters of a thermal ablation device for treating a region of interest within a subject, is provided. The method includes: iteratively adjusting initial values of the treatment parameters based on a difference between the predicted effect of the treatment parameters on the region of interest predicted by a relatively less computationally-expensive model, and a desired effect of the treatment parameters on the region of interest, to provide the optimized values of the treatment parameters; intermittently inputting the adjusted values of the treatment parameters into a relatively more computationally-expensive model; and updating the relatively less computationally-expensive model, and/or a mapping between the values of the parameters inputted into the models, such that the predicted effects of both models on the region of interest more closely match one another.

15 Claims, 5 Drawing Sheets

(56) References Cited

U.S. PATENT DOCUMENTS

| | | | | |
|---|---|---|---|---|
| 2020/0022649 | A1 * | 1/2020 | Rodriguez | A61B 5/4878 |
| 2021/0038314 | A1 * | 2/2021 | Wibowo | A61B 18/04 |
| 2021/0401502 | A1 * | 12/2021 | Liu | A61B 34/10 |
| 2022/0176155 | A1 * | 6/2022 | Isola | A61B 34/10 |

OTHER PUBLICATIONS

Mattavelli M. et al., "A New Approach to Piecewise Linear Modeling of Time Series", 1996 IEEE Digital Signal Processing Workshop Proceedings, pp. 502-505, Sep. 1996.

Kumar P. et al., "Non-Linear Dual-Phase-Lag Model for Analyzing Heat Transfer Phenomena in Living Tissues During Thermal Ablation", Journal on Thermal Biology, vol. 60, pp. 204-212, 2016.

Pennes H.H. et al., "Analysis of Tissue and Arterial Blood Temperatures in the Resting Human Forearm", Journal of Applied Physiology, vol. 1, No. 2, pp. 93-122, 1948.

Nocedal J. et al., "Large-Scale Unconstrained Optimization", In Numerical Optimization. Springer Series in Operations Research and Financial Engineering, Chapter7, pp. 164-192, Springer, 2006.

Tolle K. et al., "Efficient Therapy-Planning via Model Reduction for Laser-Induced Thermotherapy", In: Faragó, I., Izsák, F., Simon, P. (eds) Progress in Industrial Mathematics at ECMI 2018. Mathematics in Industry(), vol. 30. Springer, Cham., 2019.

Bakr M. H. Et Bal., "An Introduction to the Space Mapping Technique", Optimization and Engineering, vol. 2, Issue 4, pp. 369-384, 2001.

* cited by examiner

OPTIMIZATION IN ABLATION TREATMENT PLANNING

TECHNICAL FIELD

The present disclosure relates to determining treatment parameters of a thermal ablation device for treating a region of interest. A computer-implemented method, a processing arrangement, a system, and a computer program product, are disclosed.

BACKGROUND

The aim of thermal ablation cancer therapy is to bring a tumorous lesion to a certain temperature level such that tumour cells are lethally damaged. For example, needle-based thermal ablations utilize a miniature heating or cooling device that is mounted at the tip of a percutaneous needle. The needle is inserted into the tumorous region in a predefined way. Correctly positioned, the device is operated for a predefined time with a predefined input power to create an ablation region of desirable size. For thermal heating procedures there are e.g. needle-based microwave "MW" devices and radio frequency "RF" devices. Tissue freezing can be achieved by means of cryo-ablation needle devices. In tissue heating devices, two physical effect contribute to the temperature increase in tissue: a) direct heating-up at places where the electromagnetic field of the device is active; b) via thermal diffusion that propagates the higher temperature from the heating position to the more distant, and lower temperature, tissue regions. A cooling and temperature conservation effect happens at the surrounding of vessels that carry the blood at 37° C. body temperature.

Typically, the time dependent temperature in tissue is modelled using the bio-heat-differential equation introduced by Pennes in a document entitled "Analysis of Tissue and Arterial Blood Temperatures in the Resting Human Forearm", Journal of Applied Physiology, vol. 1, no. 2, pp 93-122, 1948, such that temperature in tissue can be predicted:

$$\rho c_p \partial_t T - \nabla(k_{ti} \nabla T) + \omega_{bl}(T - T_{core}) = Q, \qquad \text{Equation 1}$$

In Equation 1, T denotes the time-dependent spatial temperature distribution and $T_{core}$ is the constant body temperature, assumed to be 37° C. Q is the thermal energy source distribution due to the positioning and the input power of the ablation device. The other quantities denote tissue specific properties: $k_{ti}$ is the thermal conductivity, $w_{bl}$ is the blood perfusion parameter. ρ represents the tissues density, and $c_p$ represents the tissue heat capacity.

However, there remains room for improvements in determining treatment parameters of thermal ablation devices for treating regions of interest.

SUMMARY

The invention is defined by the claims.

According to one aspect of the present disclosure, a computer-implemented method of providing optimized values of one or more treatment parameters of a thermal ablation device for treating a region of interest within a subject, is provided. The method includes:

- receiving a relatively less computationally-expensive model and a relatively more computationally-expensive model, the models each describing a predicted effect of the one or more treatment parameters on the region of interest;
- receiving one or more treatment goals describing a desired effect of the one or more treatment parameters on the region of interest; and
- generating optimized values for the one or more treatment parameters by:
  - inputting one or more initial values of the one or more treatment parameters into the relatively less computationally-expensive model;
  - iteratively adjusting the one or more initial values of the one or more treatment parameters based on a difference between the predicted effect of the one or more treatment parameters on the region of interest predicted by the relatively less computationally-expensive model, and the desired effect of the one or more treatment parameters on the region of interest, to provide the optimized values of the one or more treatment parameters;
  - intermittently inputting the adjusted values of the one or more treatment parameters into the relatively more computationally-expensive model; and
  - updating the relatively less computationally-expensive model such that the predicted effects of both models on the region of interest more closely match one another; and/or
  - updating a mapping between the adjusted values of the one or more treatment parameters inputted into the relatively more computationally-expensive model and the values of the one or more corresponding adjusted treatment parameters inputted into the relatively less computationally-expensive model, such that the predicted effects of both models on the region of interest more closely match one another, and wherein the relatively less computationally-expensive model is provided by a deep learning model or a deep-learning enhanced projection-based model.

Further aspects, features, and advantages of the present disclosure will become apparent from the following description of examples, which is made with reference to the accompanying drawings.

DETAILED DESCRIPTION

Figure 1:
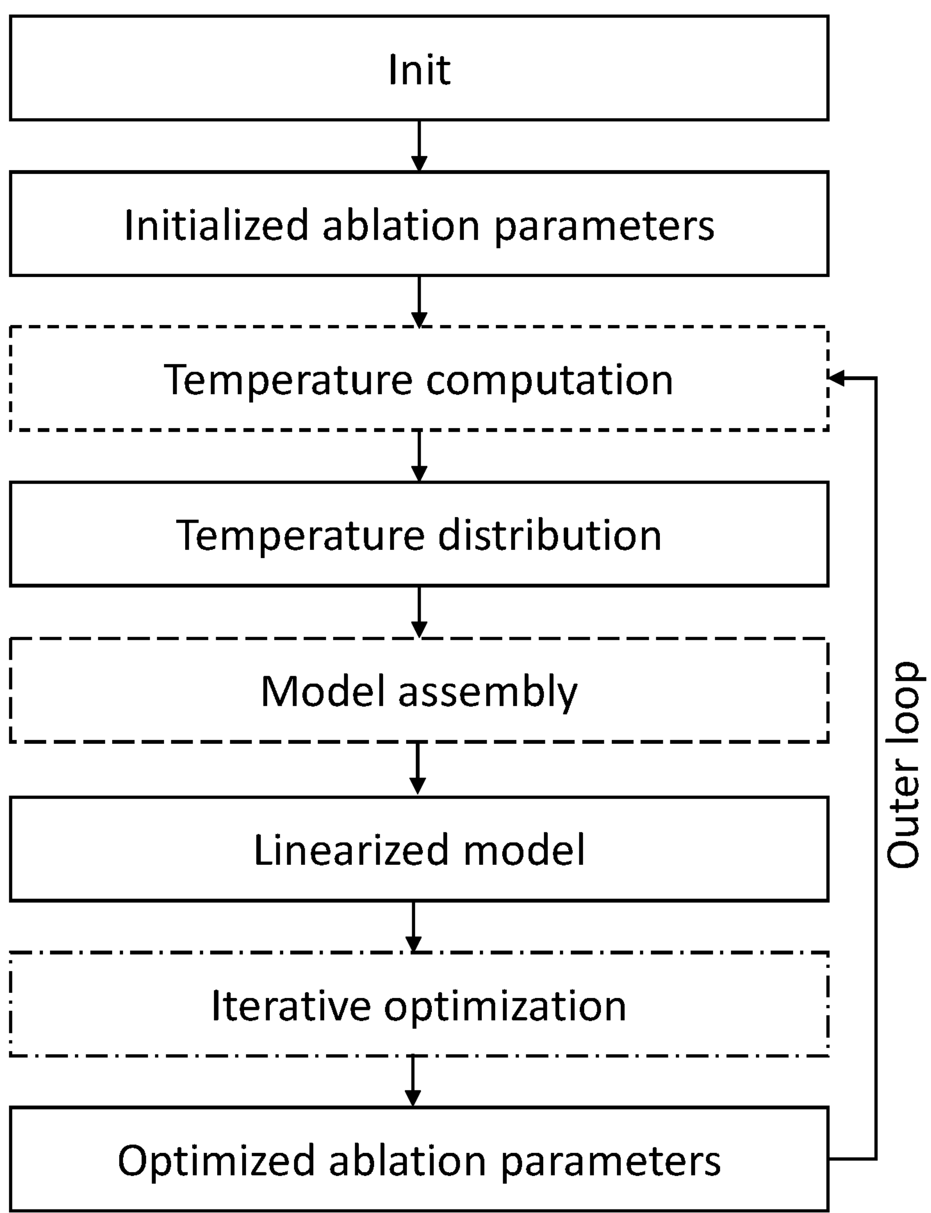
FIG. 1 illustrates a schematic drawing of workflow of an optimization approach for finding optimal ablation device input parameters that includes updating a relatively less computationally-expensive model, in accordance with a first aspect of the present disclosure.

Examples of the present disclosure are provided with reference to the following description and figures. In this description, for the purposes of explanation, numerous specific details of certain examples are set forth. Reference in the specification to "an example", "an implementation" or similar language means that a feature, structure, or characteristic described in connection with the example is included in at least that one example. It is also to be appreciated that features described in relation to one example may also be used in another example, and that all features are not necessarily duplicated in each example for the sake of brevity. For instance, features described in relation to a computer implemented method, may be implemented in a computer program product, and in a system, in a corresponding manner.

It is noted that the computer-implemented methods disclosed herein may be provided as a non-transitory computer-readable storage medium including computer-readable instructions stored thereon, which, when executed by at least one processor, cause the at least one processor to perform the method. In other words, the computer-implemented methods may be implemented in a computer program product. The computer program product can be provided by dedicated hardware, or hardware capable of running the software in association with appropriate software. When provided by a processor, the functions of the method features can be provided by a single dedicated processor, or by a single shared processor, or by a plurality of individual processors, some of which can be shared. The functions of one or more of the method features may for instance be provided by processors that are shared within a networked processing architecture such as a client/server architecture, the internet, or the cloud. The explicit use of the terms "processor" or "controller" should not be interpreted as exclusively referring to hardware capable of running software, and can implicitly include, but is not limited to, digital signal processor "DSP" hardware, read only memory "ROM" for storing software, random access memory "RAM", a non-volatile storage device, and the like. Furthermore, examples of the present disclosure can take the form of a computer program product accessible from a computer-usable storage medium, or a computer-readable storage medium, the computer program product providing program code for use by or in connection with a computer or any instruction execution system. For the purposes of this description, a computer-usable storage medium or a computer readable storage medium can be any apparatus that can comprise, store, communicate, propagate, or transport a program for use by or in connection with an instruction execution system, apparatus, or device. The medium can be an electronic, magnetic, optical, electromagnetic, infrared, or a semiconductor system or device or propagation medium. Examples of computer-readable media include semiconductor or solid state memories, magnetic tape, removable computer disks, random access memory "RAM", read-only memory "ROM", rigid magnetic disks and optical disks. Current examples of optical disks include compact disk-read only memory "CD-ROM", compact disk-read/write "CD-R/W", Blu-Ray™ and DVD.

As mentioned above, typically, the time dependent temperature in tissue is modelled using the bio-heat-differential equation, Equation 1, in order to determine the effects of thermal ablation devices. In Equation 1, T denotes the time-dependent spatial temperature distribution and $T_{core}$ is the constant body temperature, assumed to be 37° C. Q is the thermal energy source distribution due to the positioning and the input power of the ablation device. The other quantities denote tissue specific properties: $k_{ti}$ is the thermal conductivity, $w_{bl}$ is the blood perfusion parameter. ρ represents the tissues density, and $c_p$ represents the tissue heat capacity. All these physiological parameters vary between different organs and different tissue types. In general, the tissue parameter values may change with temperature. However, as long as the change in tissue temperature is in a moderate range, many modelling approaches assume the parameter values are temperature independent; this is often the case e.g. when modeling thermal ablation with e.g. RF devices. In RF ablations, the volumetric size of the heat source area is rather small and the achieved temperature increase is moderate (typically below 100° C.) such that the final ablation zone is formed after rather long time mainly based on the effects thermal diffusion. When using MW ablations, the achieved temperatures are typically much higher (up to 130° C.-150° C.) and the raise is much faster, such that the temperature dependent change of tissue parameter values in Equation 1 including a change of phase (i.e. boiling) may be considered for an accurate prediction of ablation.

In numerical simulations of ablation procedures, the thermal model of Equation 1 is discretized in time and space yielding equation systems that are solved for each time point to compute the tissue temperature distribution over time.

For linear modelling (e.g. used for simulating RF ablations), all the tissue parameters $k_{ti}$, $w_{bl}$, ρ, $c_p$ in the thermal model can be obtained once and a linear equation system is solved for each time step. This is an operation that has rather moderate computational costs. By contrast, the handling of temperature dependent tissue parameters in MW ablation simulations makes the computations more computationally-expensive, because: a) a non-linear equation system are to be solved in each time step (which typically requires more complex solver methods, e.g. iterative ones); b) temperature dependent tissue parameters are to be repeatedly assembled (at least once) for each time step. These differences in required complexity of thermal modelling have a strong impact on its applicability for the prediction of ablation zones, and even more for finding optimal ablation parameters.

With the availability of a thermal tissue model (and a corresponding tissue damage model) the impact of chosen input parameters of the ablation device to the expected volumetric size and location of the ablation zone can be predicted. However, manual tweaking of ablation parameters by the user until the ablation zone sufficiently covers the tumor region can be tedious manual procedure.

In optimization-based automated treatment planning the desired size and position of an ablation zone is prescribed by the user and the planning system generates the optimal input parameters. Such optimal ablation parameters might include device position, device orientation, number of devices, ablation time, and input power to device.

There are certain run time constraints for executing such a parameter estimation, in particular when ablation parameters are estimated during operation. Hence, a high computational speed is used for the optimizer. Typically, iterative mathematical optimization methods (e.g. gradient based optimization, quasi-Newton methods) which repeatedly evaluate the thermal model are employed for parameter estimation. For microwave ablations and cryo-ablations a non-linear thermal modelling approach is used for accurate temperature prediction. However, usage of such runtime computationally-expensive model inside an iterative optimization method appears prohibitive in many practical application scenarios.

This is more stringent than the situation of treatment plan optimization for RF ablations. There, the optimization approach can use a much wider range of typical device operation settings in a linear thermal model. Such RF models can be evaluated very rapidly multiple times inside the mathematical optimizer.

The present disclosure addresses the problem of very long runtime in an ablation parameter optimizer that employs a computationally-expensive nonlinear thermal model. It enables a practical clinical application with accurate ablation parameter estimation in a microwave/cryo-ablation context.

In accordance with the present disclosure, high speed parameter optimization is provided by using a relatively less complex, and therefore fast-to-evaluate, model, inside relatively more complex iterative optimizer model. The internal parameters of the less complex model are adjusted from extracted information from a more complex, non-linear thermal model that is more computationally-expensive. Such model parameter adjustment ensures that the less complex model does not deviate too much from the more complex model over the course of iterations in the optimization process. The key with such an optimization approach is to evaluate the more complex non-linear model as few times as possible because this is more computationally-expensive.

FIG. 1 illustrates a schematic drawing of workflow of an optimization approach for finding optimal ablation device input parameters that includes updating a relatively less computationally-expensive model, in accordance with a first aspect of the present disclosure. In FIG. 1, the Temperature computation step (outlined with short dashes) provides an accurate computation of the transient temperature distribution using a non-linear thermal model. In the Model assembly step (outlined with long dashes) information is extracted from the transient temperature distribution to set-up a less complex linear model. In the Iterative optimization step (with dash-dot outline) an iterative optimization is performed that evaluates the linear model multiple times to obtain optimal ablation parameters.

With reference to FIG. 1, in order to build the ablation parameter optimization, the following three steps are proposed. 1: An accurate computation of temperature (Temperature computation step): this step computes the transient temperature distribution for a given set of ablation device parameters (e.g. device input power). For MW ablations, such computation is based on the non-linear thermal model. Evaluation of such non-linear model might use iterative methods and successive re-computation of temperature dependent tissue parameters, making this a computationally-expensive step. Typically, this step is already available in systems that support ablation procedures and include a prediction/simulation of temperature distributions due to an ablation device. 2. Assembly of less complex model (Model assembly step): this step extracts information from the non-linear model used in the Temperature computation step and from the temperature distribution computed accordingly. This information is used to assemble a less-complex thermal model to be used in the iterative optimization. Some pre-computations might be carried out in this step in order to reduce subsequently repeated computations in the Iterative optimization step. The model assembly typically creates a linear or an affine thermal model that relates some ablation parameter to an approximate resulting temperature distribution. 3. Iterative (parameter) optimizer (Iterative optimisation step): for a given prescription of target temperatures the numerical optimizer finds the best ablation parameters using the less-complex model. Typically a gradient based iterative optimizer (e.g. quasi-Newton methods, L-BFGS, such as that disclosed in a document by J. Nocedal and S. J. Wright, Numerical Optimization, Springer, 2006) is applied that successively evaluates the less-complex thermal model for different ablation parameters. The main computational load in this step arises from evaluating the less-complex thermal model and from computing the gradient with respect to ablation parameters, which may incur a similar effort as model evaluation. The ablation parameters found in this optimization step are used in a feedback loop as a new reference input for the accurate Temperature computation step.

Temperature Computation Step in FIG. 1:

A computer based formulation of the thermal model uses a discretization of time and space of Equation 1, yielding an equation system to be solved for each time step:

$$[\rho(T^n)c_p(T^n)M + dt(k_{ti}(T^n)S + \omega_{bl}(T^n)M)](T^n - T_{core}) = dtMQ^n + \rho(T^n)c_p(T^n)M\left(T^{n-1} - T_{core}\right) \qquad \text{Equation 2}$$

Where M and S denote the spatial discretization matrices in a finite element method (FEM) approach, dt is the time step size. For MW ablations the tissue parameters $k_{ti}$, $w_{bl}$, ρ, $c_p$ depend on the temperature $T^n$ at the current time step n, as well as the heat source (that might depend on temperature related electro-magnetic tissue absorption), such that Equation 2 represents a non-linear equation system. As indicated by the Temperature computation step in FIG. 1, a non-linear equation system solver is used to compute the temperature $T^n$ at each time step recursively for a given input $Q^n$.

The ablation parameters (e.g. device input power, ablation duration, etc.) which are subject to optimization are structurally encoded into the input $Q^n$; e.g. a certain input power represents a constant scaling factor in all $Q^n$. In the first phase of optimization, the ablation parameters are initialized according to some setting strategy; this corresponds to the usage of an initial input heat $Q^n$. In the later phases, the ablation parameters are generated by the numerical optimization module (Iterative optimization step) which are then fed-back as new input to the accurate temperature computation.

Model Assembly Step in FIG. 1

In order to have a high speed in the process of numerical optimization, a less complex, and therefore faster-to-evaluate model is used inside the optimizer (as compared to the accurate temperature computation). One possible formulation of such model for computing the temperature $T^n$ at each time step is as follows; similar to the single step optimization approach proposed for MW ablations in European patent publication EP3718599A1:

$$A(T^n - T_{core}) = CQ^n + B\left(T^{n-1} - T_{core}\right) + p^n \qquad \text{Equation 3}$$

This is an affine model with global and constant model parameter matrices A, B and C as well as time dependent parameter $p^n$. However, other types of simplified models are also suitable. Here, for a given input heat $Q^n$ the temperature at each time point can be evaluated rapidly by solving a linear equation system.

In the Model assembly step in FIG. 1, the model parameters of Equation 3 are generated for a specific value of the input $Q^n$ based on the nonlinear thermal model. One possible way to compute the global model parameter matrices A, B and C in Equation 3 is to derive these as temporal averages from the corresponding expressions in Equation 2; e.g. for the matrix A:

$$A = \frac{1}{N}\sum_{n=1}^{N} \rho(T^n)c_p(T^n)M + dt(k_{ti}(T^n)S + \omega_{bl}(T^n)M) \quad \text{Equation 4}$$

The other global parameters B and C can be obtained in a similar way by computing corresponding temporal averages accordingly. The time dependent parameters $p^n$ in Equation 3 are set in a way such that for a given $Q^n$ the temperature $T^n$ in Equation 3 equals the corresponding temperature in the original Equation 2. Such setting of $p^n$ at each time point guaranties that the simple model in Equation 3 yields the same temperature values as the accurate model in Equation 2 for a given reference input heat $Q^n$. For different values of the input heat both models typically yield differing temperatures; however as long as the input heat does not deviate too much from the reference value the temperatures generated by the original model and by the simplified model should not differ too much.

Two modifications in the model assembly are contemplated for further speeding-up the optimization procedure:

a) Typically, the creation of temperature dependent tissue parameters $k_{ti}$, $W_{bl}$, ρ, $c_p$ for each time point n in Equation 4 is a computationally-expensive step which also affects the overall computation time in optimization. One way to speed-up the computations required in Equation 4 is to use an approximation of the temporal averaging that takes into account less time steps than the original N steps. Because the expected change of temperature happens slowly over time it turns out that taking the sum in Equation 4 only for every second or every third time point does not alter the finally estimated value for A; the same is valid for similar approximations when computing B and C.

b) Another modification requires some precomputations to make the evaluation of the simplified model in Equation 3 of all time steps faster. However, this modification is only valid when optimizing for ablation parameters that have a linear relation to the input heat $Q^n$. This property holds e.g. for the input power of the ablation device which resembles a simple scaling of the input heat. In this case the temperature all time points can be computed in a very fast way directly from the ablation parameter (named p):

$$\begin{pmatrix} T^1 \\ \vdots \\ T^N \end{pmatrix} = D \cdot p + \begin{pmatrix} T_0^1 \\ \vdots \\ T_0^N \end{pmatrix} \quad \text{Equation 5}$$

Here, the matrix D and all offset temperatures $T_0^1, \ldots, T_0^N$ can be precomputed from the parameters in Equation 3. These precomputations are part of the Model assembly step in FIG. 1, and might slightly prolong the computational effort there. However, a large improvement in computational speed is gained (compared to the implementation in Equation 3) when such an approach for implementing the simplified model is used in the iterative numerical optimizer.

Iterative Optimisation Step in FIG. 1

Typically, an iterative numerical optimization method (e.g. Quasi Newton methods, L-BFGS) is utilized to find the optimal ablation parameters which yield temperature values $(T^1, \ldots, T^N)$ that are as close as possible to the prescribed target temperatures in the ablation plan (see Iterative optimization step in FIG. 1). Such iterative optimizer follows a certain path of different ablation parameters p by generating the corresponding input heat $(Q^1, \ldots, Q^N)$ and using the simplified thermal model of Equation 3 to compute the temperature distribution $(T^1, \ldots, T^N)$ accordingly. For each value of p on the optimizer's search path the simplified thermal model is applied such that multiple evaluations of Equation 3 are required. Here the full benefit in terms of computational effort is exploited because the usage of the model in Equation 3 is much more efficient than usage of the non-linear model of Equation 2. The more iteration steps are used in the optimizer the larger the gain in computation time (compared to the usage of Equation 2).

After termination, the optimizer yields the optimal (in the sense of the simplified thermal model) ablation parameters p which in turn correspond to an optimal heat $(Q^1, \ldots, Q^N)$ These optimized parameters are fed back and are used as input to the accurate temperature computation (Temperature computation step in FIG. 1). Such feedback resembles the outer loop in the overall optimization procedure as depicted in FIG. 1. As the accurate temperature computation as is a computationally-expensive step the number of outer loop iterations should be kept as small as possible. The iterations of the outer loop are thus performed intermittently, and these iterations may be periodical, or aperiodic.

Figure 2:
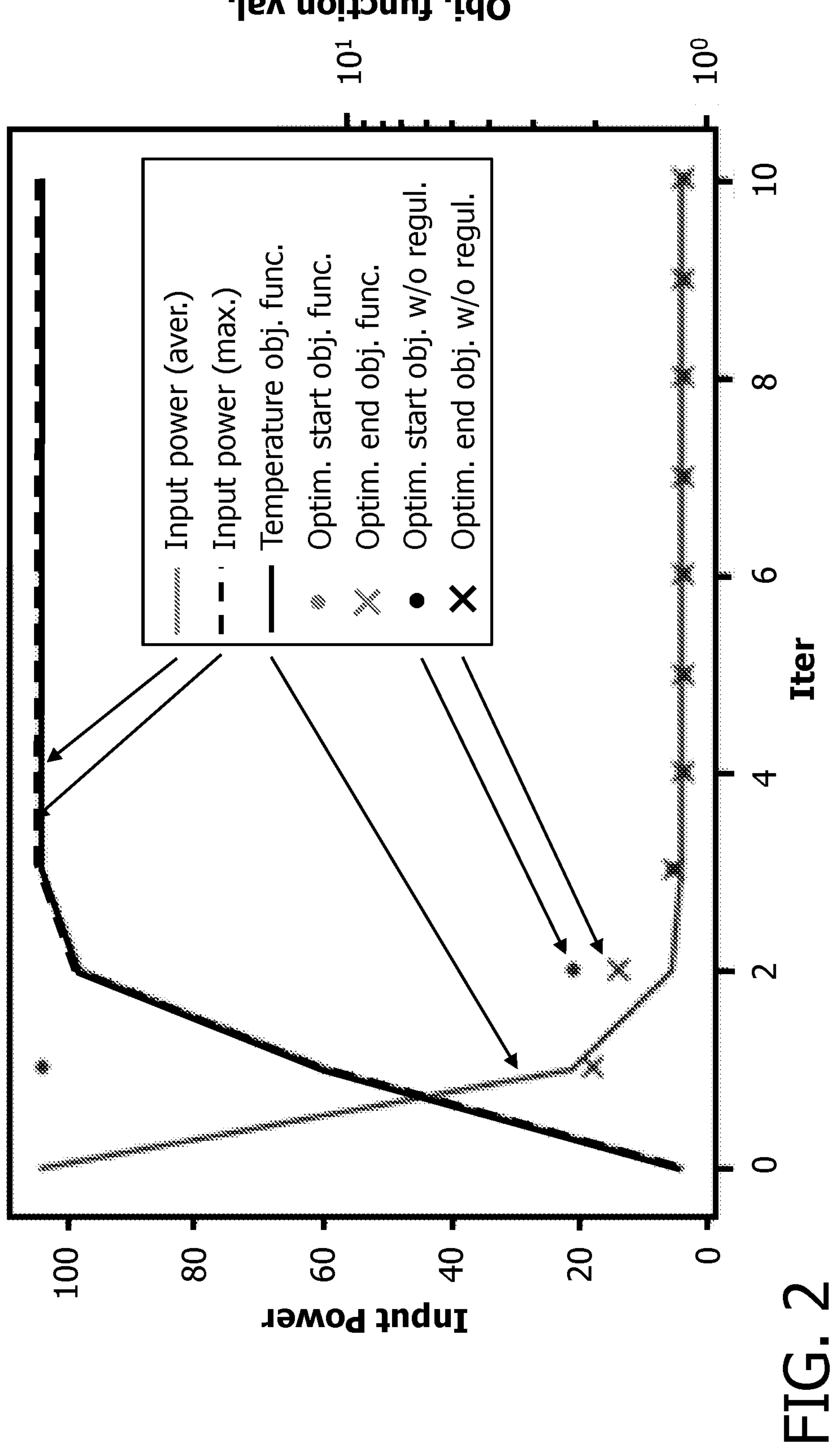
FIG. 2 is a graph illustrating an example for optimization of ablation input power parameter using 10 iteration steps (Iter) in the outer loop, in accordance with the first aspect of the present disclosure.

FIG. 2 is a graph illustrating an example for optimization of ablation input power parameter using 10 iteration steps (Iter) in the outer loop, in accordance with the first aspect of the present disclosure. Step 0 in FIG. 2 corresponds to the initial parameter settings. The upper curve on the right side of FIG. 2 labelled "Input power (aver)" and "Input power (max)", shows the power value found by the optimizer in each step of the outer loop. The lower curve on the right side of FIG. 2 labelled "Temperature Obj. func." shows the objective function value (i.e. distance between the optimized temperatures compared to the prescribed target temperatures). The dots and the crosses represent the initial and the final objective function value found be the optimizer using the less complex thermal model of Equation 3. The lower curve on the right side of FIG. 2 labelled "Temperature Obj. func." represents the objective function value when using the optimized ablation parameters in the accurate non-linear model of Equation 2.

FIG. 2 depicts a real example for ablation input power optimization with 10 iteration steps in the outer loop. In FIG. 2, the optimal ablation input power value is already reached after 3 steps in the outer loop. The upper curve on the right side of FIG. 2 shows the value of ablation power found by the optimizer at each step of the outer loop. The lower curve on the right side of FIG. 2, as well as the points represented by the crosses and dots in FIG. 2 represent the objective function value of the optimized temperatures. Here the squared difference between the optimized temperatures and the prescribed target temperatures is used as objective function. For a given step in the outer loop the dot and the cross represent the objective function values corresponding to the initial power value and the optimized power value, respectively, found by the iterative optimizer that uses the less complex thermal model (Iterative optimization step in FIG. 1). The objective function values on the curve on the right side of FIG. 2 correspond to the temperature generated by the accurate non-linear thermal model when using the optimized ablation power value as input (Temperature computation step in FIG. 2). It was observed in all evaluated scenarios that optimization of the temperature in this simplified model yields a corresponding improvement of the objective function value when using the accurate model. Such property makes the invented optimization approach efficient and has a practical application because e.g. in this example the computationally-expensive non-linear model is evaluated only three times only before reaching the optimal solution.

Figure 3:
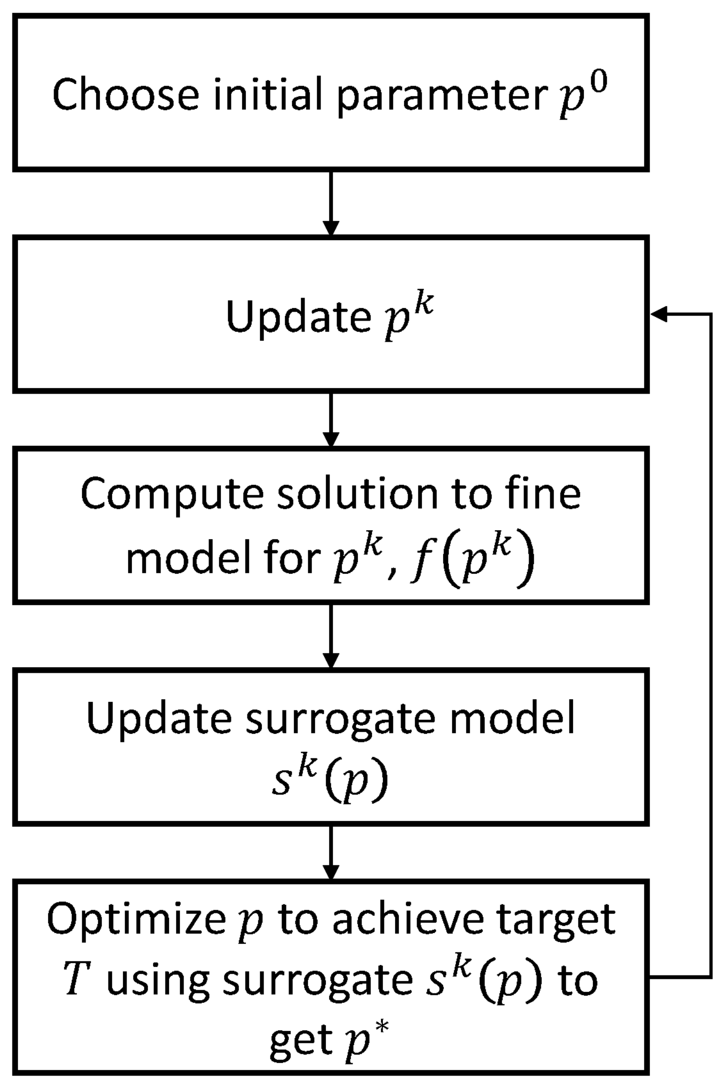
FIG. 3 illustrates a schematic drawing of workflow of an optimization approach for finding optimal ablation device input parameters that includes updating a mapping of the values of treatment parameters, in accordance with a second aspect of the present disclosure.

FIG. 3 illustrates a schematic drawing of workflow of an optimization approach for finding optimal ablation device input parameters that includes updating a mapping of the values of treatment parameters, in accordance with a second aspect of the present disclosure. In contrast to the approach of FIG. 1 in which the relatively less computationally-expensive model is updated such that the predicted effects of both models on the region of interest more closely match one another, in FIG. 3, a mapping between the adjusted values of the one or more treatment parameters inputted into the relatively more computationally-expensive model and the values of the one or more corresponding adjusted treatment parameters inputted into the relatively less computationally-expensive model, is updated, such that the such that the predicted effects of both models on the region of interest more closely match one another.

Figure 4:
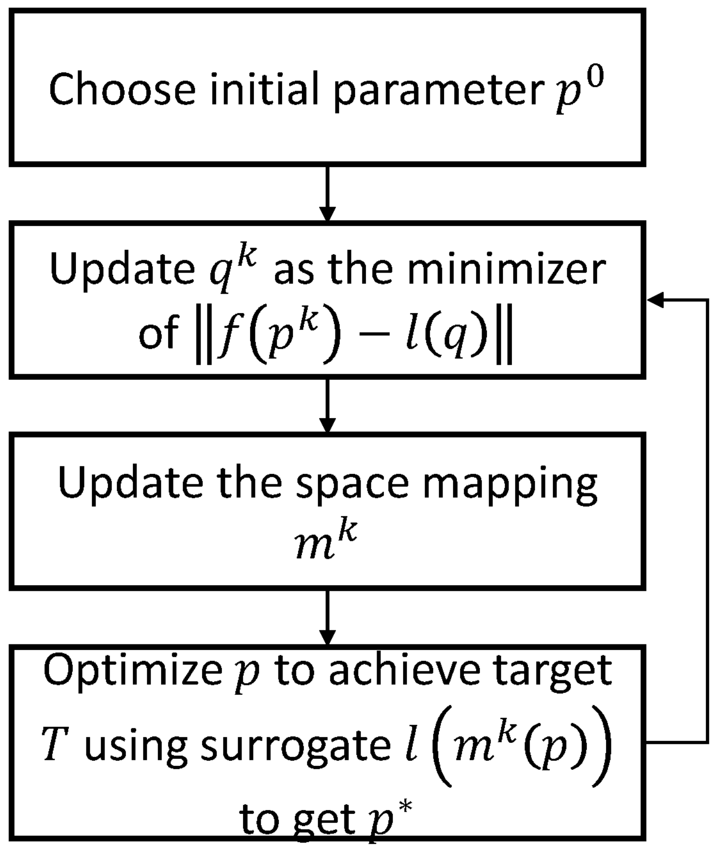
FIG. 4 illustrates a schematic drawing that includes details for updating a mapping of the values of treatment parameters, in accordance with a second aspect of the present disclosure.

In the approach illustrated in FIG. 3, it is assumed that $p \in \mathcal{P}$ is the parameter that is to be optimized, and that there are two models available: a relatively more computationally-expensive model, or in other words, a fine and accurate model $f: \mapsto_f \rightarrow \mathbb{R}^n$, that maps $p \in \mapsto_f \mapsto f(p)$, and a relatively less computationally-expensive model, or in other words a coarse and less accurate model $l: \mapsto_c \rightarrow \mathbb{R}^n$, that maps $q \in \mapsto_c \mapsto l(q)$. It is also assumed that there is a parameter mapping $m: \mapsto_f \rightarrow \mapsto_c$, s.t. $f(p) \approx l(m(p))$. In the first aspect, this is the identity, and $\mapsto_f = \mapsto_c$ and in every outer loop iteration the coarse model is being updated. In the second aspect illustrated in FIG. 3, it is assumed that the fine model $f: \mapsto \rightarrow \mathbb{R}^n$ can be approximated locally in the parameter space by a surrogate model $s: \mapsto \rightarrow \mathbb{R}^n$. For example $s = l \circ m$, where $l: \mapsto_c \rightarrow \mathbb{R}^n$ is the linearization of the model f, and $m: \mapsto_f \rightarrow \mapsto_c$, is the parameter space mapping. In FIG. 3, the step to update the surrogate model $s^k$ is then the updated space mapping $m^k$. An example of performing updating a parameter space mapping is illustrated in FIG. 4, which illustrates a schematic drawing that includes details for updating a mapping of the values of treatment parameters, in accordance with a second aspect of the present disclosure. With reference to FIG. 4, let $p \in \mathcal{P}$ be the parameter that it is desired to optimize. Assume again that two models are available: the fine and accurate model $f: \mathcal{P}_f \rightarrow \mathbb{R}^n$, that maps $p \in \mathcal{P}_f \mapsto f(p)$, and the coarse and less accurate model $l: \mathcal{P}_c \rightarrow \mathbb{R}^n$, that maps $q \in \mathcal{P}_c \mathcal{P}\, l(q)$. Assume that there is a parameter mapping $m: \mathcal{P}_f \rightarrow \mathcal{P}_c$, s.t. $f(p) \approx l(m(p))$. Let $T \in \mathbb{R}^n$ be the target of the optimization problem. Using the space mapping method, it is assumed that the coarse model is fixed over the whole parameter space $\mathcal{P}_f$, and the mapping m is updated in every outer loop update of the parameter optimization problem. Further details on the technique illustrated in FIG. 4 are described in a document by Tolle, K., and Marheineke, N., entitled "Efficient Therapy-Planning via Model Reduction for Laser-Induced Thermotherapy", published in Progress in Industrial Mathematics at ECMI 2018, Mathematics in Industry 30, pages 207-213, I. Faragó et al. (eds.).

Figure 5:
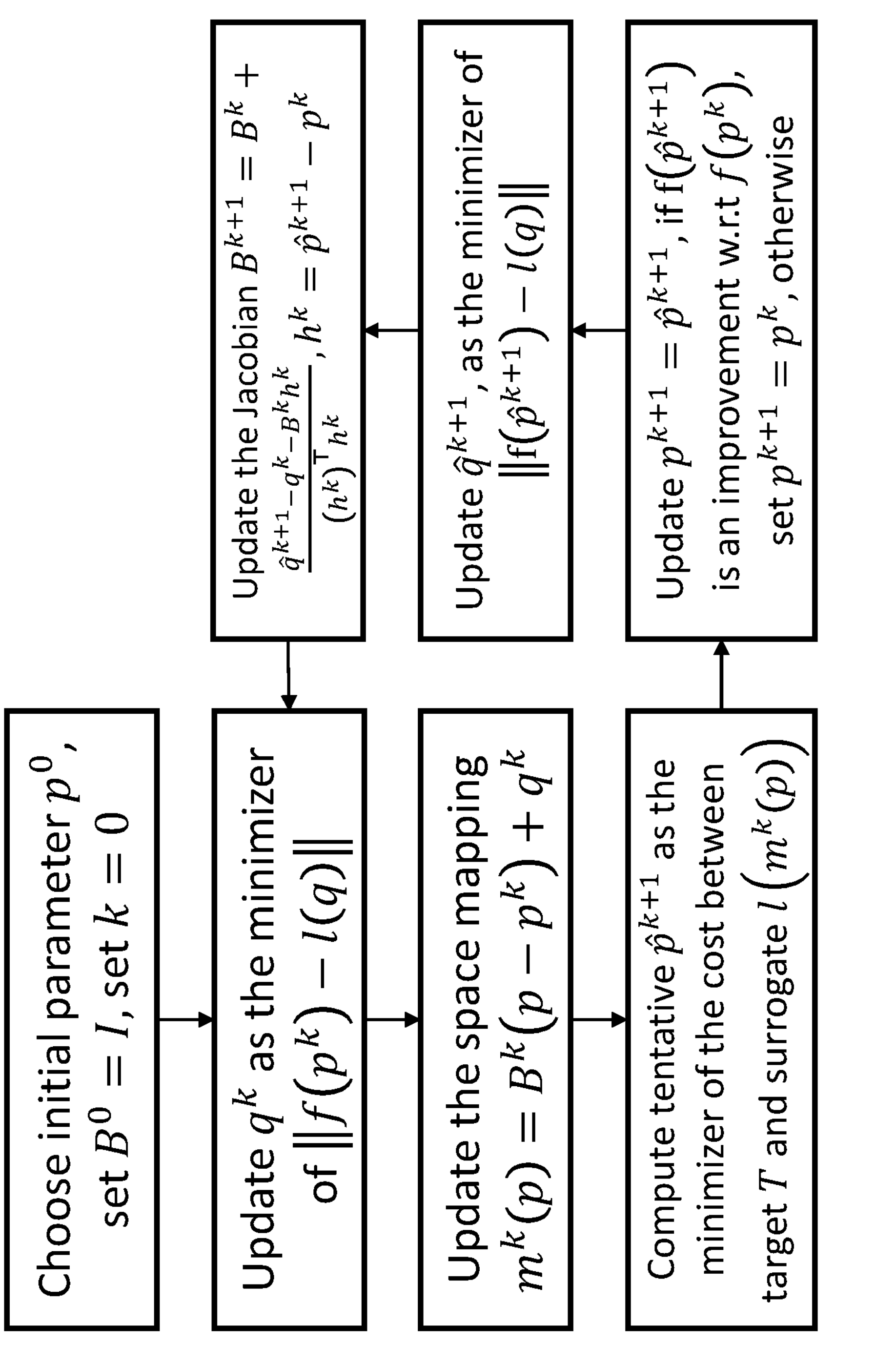
FIG. 5 illustrates a schematic drawing that includes further details for updating a mapping of the values of treatment parameters, in accordance with a second aspect of the present disclosure.

The step to update the mapping in FIG. 4 may be performed in different ways, one of which is illustrated in FIG. 5, and which illustrates a schematic drawing that includes further details for updating a mapping of the values of treatment parameters, in accordance with a second aspect of the present disclosure. Further details on the technique illustrated in FIG. 5 are described in a document by Bakr, M. H., Bandler, J. W., Madsen, K. et al. entitled "An Introduction to the Space Mapping Technique", Optimization and Engineering 2, 369-384 (2001).

A combination of the approaches described with reference to FIG. 1 and FIG. 3 may also be used. For example, in some iterations the outer loop in FIG. 1 and FIG. 3, may include both updating the relatively less computationally-expensive model and updating the mapping of the parameters, and in other iterations only one of these may be updated.

The above examples are to be understood as illustrative of the present disclosure, and not restrictive. Further examples are also contemplated. For instance, the examples described in relation to computer-implemented methods, may also be provided by the computer program product, or by the computer-readable storage medium, or by a system that includes one or more processors configured to carry out the methods, in a corresponding manner. It is to be understood that a feature described in relation to any one example may be used alone, or in combination with other described features, and may be used in combination with one or more features of another of the examples, or a combination of other examples. Furthermore, equivalents and modifications not described above may also be employed without departing from the scope of the invention, which is defined in the accompanying claims. In the claims, the word "comprising" does not exclude other elements or operations, and the indefinite article "a" or "an" does not exclude a plurality. The mere fact that certain features are recited in mutually different dependent claims does not indicate that a combination of these features cannot be used to advantage. Any reference signs in the claims should not be construed as limiting their scope.

The invention claimed is:

1. A computer-implemented method of providing optimized values of one or more treatment parameters of a thermal ablation device for treating a region of interest within a subject, the method comprising:

receiving a relatively less computationally-expensive model and a relatively more computationally-expensive model, the models each describing a predicted effect of the one or more treatment parameters on the region of interest;

receiving one or more treatment goals describing a desired effect of the one or more treatment parameters on the region of interest; and generating optimized values for the one or more treatment parameters by:

inputting one or more initial values of the one or more treatment parameters into the relatively less computationally-expensive model;

iteratively adjusting the one or more initial values of the one or more treatment parameters based on a difference between the predicted effect of the one or more treatment parameters on the region of interest predicted by the relatively less computationally-expensive model, and the desired effect of the one or more treatment parameters on the region of interest, to provide the optimized values of the one or more treatment parameters;

intermittently inputting the adjusted values of the one or more treatment parameters into the relatively more computationally-expensive model; and updating the relatively less computationally-expensive model such that the predicted effects of both models on the region of interest more closely match one another; and/or updating a mapping between the adjusted values of the one or more treatment parameters inputted into the relatively more computationally-expensive model and the values of the one or more corresponding adjusted treatment parameters inputted into the relatively less computationally-expensive model, such that the predicted effects of both models on the region of interest more closely match one another, and wherein the relatively less computationally-expensive model is provided by a deep learning model or a deep-learning enhanced projection-based model.

2. The computer-implemented method according to claim 1, wherein the updating the relatively less computationally-expensive model such that the predicted effects of both models on the region of interest more closely match one another, comprises iteratively executing the relatively more computationally-expensive model to determine the effect of the relatively more computationally-expensive model on the region of interest.

3. The computer-implemented method according to claim 1, wherein the iteratively adjusting the one or more initial values of the one or more treatment parameters is performed using a gradient-based technique.

4. The computer-implemented method according to claim 1, wherein the relatively less computationally-expensive model comprises a linear model, and wherein the relatively more computationally-expensive model comprises a non-linear model.

5. The computer-implemented method according to claim 1, wherein the relatively less computationally-expensive model comprises a surrogate model computed using a projection-based method, or a surrogate model computed using a machine learning technique, or a surrogate model computed using a deep learning technique.

6. The computer-implemented method according to claim 1, wherein the optimized values of the one or more treatment parameters are provided for a plurality of time steps, and wherein the relatively less computationally-expensive model describes a predicted effect of the one or more treatment parameters on the region of interest over time, and comprises temperature-dependent thermal parameters of tissue in the region of interest that vary over time; and wherein the iteratively adjusting the one or more initial values of the one or more treatment parameters comprises executing the relatively less computationally-expensive model to determine the predicted effect of the one or more treatment parameters on the region of interest predicted by the relatively less computationally-expensive model for the plurality of time steps, and wherein the temperature-dependent thermal parameters are adjusted less frequently than at every time step.

7. The computer-implemented method according to claim 1, wherein:

the relatively more computationally-expensive model describes a predicted effect of the one or more treatment parameters on the region of interest and comprises temperature-dependent thermal parameters of tissue in the region of interest; and wherein the relatively less computationally-expensive model describes a predicted effect of the one or more treatment parameters on the region of interest and comprises temperature-independent thermal parameters of tissue in the region of interest.

8. The computer-implemented method according to claim 6, wherein the thermal parameters comprise one or more of the following for a tissue in the region of interest: a thermal conductivity, a blood perfusion parameter, a density, a heat capacity.

9. The computer-implemented method according to claim 1, wherein the relatively less computationally-expensive model is executed for effects of the one or more treatment parameters that are less than or equal to 100 degrees centigrade, and wherein the relatively more computationally-expensive model is executed for effects of the one or more treatment parameters that exceed 100 degrees centigrade.

10. The computer-implemented method according to claim 1, wherein the one or more treatment parameters include one or more of the following for the thermal ablation device: a position with respect to the region of interest, an orientation with respect to the region of interest, a power, and an activation period.

11. The computer-implemented method according to claim 1, wherein the predicted effect and/or the desired effect comprises one or more of the following for the region of interest: a temperature distribution, a damage distribution.

12. The computer-implemented method according to claim 1, wherein the generating optimized values for the one or more treatment parameters comprises executing the relatively more computationally-expensive model fewer times than executing the relatively less computationally-expensive model.

13. The computer-implemented method according to claim 1, wherein the thermal ablation device comprises: an RF ablation device, a microwave ablation device, or a cryo-ablation device.

14. The computer-implemented method according to claim 1, further comprising outputting a value representing a difference between the predicted effect of the one or more treatment parameters on the region of interest predicted by the relatively less computationally-expensive model, and the desired effect of the one or more treatment parameters on the region of interest.

15. A system for providing optimized values of one or more treatment parameters of a thermal ablation device for treating a region of interest within a subject, the system comprising one or more processors configured to:

receive a relatively less computationally-expensive model and a relatively more computationally-expensive model, the models each describing a predicted effect of the one or more treatment parameters on the region of interest;

receive one or more treatment goals describing a desired effect of the one or more treatment parameters on the region of interest; and generate optimized values for the one or more treatment parameters by:

inputting one or more initial values of the one or more treatment parameters into the relatively less computationally-expensive model;

iteratively adjusting the one or more initial values of the one or more treatment parameters based on a difference between the predicted effect of the one or more treatment parameters on the region of interest predicted by the relatively less computationally-expensive model, and the desired effect of the one or more treatment parameters on the region of interest, to provide the optimized values of the one or more treatment parameters;

intermittently inputting the adjusted values of the one or more treatment parameters into the relatively more computationally-expensive model; and updating the relatively less computationally-expensive model such that the predicted effects of both models on the region of interest more closely match one another; and/or updating a mapping between the adjusted values of the one or more treatment parameters inputted into the relatively more computationally-expensive model and the values of the one or more corresponding adjusted treatment parameters inputted into the relatively less computationally-expensive model, such that the predicted effects of both models on the region of interest more closely match one another, and wherein the relatively less computationally-expensive model is provided by a deep learning model or a deep-learning enhanced projection-based model.

* * * * *